(12) United States Patent
Mock et al.

(10) Patent No.: US 12,259,336 B2
(45) Date of Patent: Mar. 25, 2025

(54) ONLINE METHOD TO DETERMINE QUALITY STANDARDS FOR INCOMING WOOD CHIPS TO A PAPERMILL

(71) Applicant: Event Capture Systems, Inc., Mint Hill, NC (US)

(72) Inventors: Brian James Mock, Mint Hill, NC (US); John Graves Larkin, Gastonia, NC (US); Akhil Kumar, Bangalore (IN); David Hirvonen, Brooklyn, NY (US); Chris Giroux, British Columbia (CA)

(73) Assignee: Event Capture Systems, Inc., Mint Hill, NC (US)

( * ) Notice: Subject to any disclaimer, the term of this patent is extended or adjusted under 35 U.S.C. 154(b) by 468 days.

(21) Appl. No.: 17/403,051

(22) Filed: Aug. 16, 2021

(65) Prior Publication Data

US 2021/0372940 A1 Dec. 2, 2021

Related U.S. Application Data

(63) Continuation of application No. PCT/US2020/018236, filed on Feb. 14, 2020.
(Continued)

(51) Int. Cl.
*G01N 21/898* (2006.01)
*G06F 3/048* (2013.01)
(Continued)

(52) U.S. Cl.
CPC ......... *G01N 21/8986* (2013.01); *G06F 3/048* (2013.01); *G06F 16/51* (2019.01);
(Continued)

(58) Field of Classification Search
CPC ... G01N 21/8986; G06F 16/583; G06F 16/51; G06F 3/048; G06Q 50/04; G06T 7/0004; G06T 2200/24; G06T 2207/30161
(Continued)

(56) References Cited

U.S. PATENT DOCUMENTS

| 6,175,092 B1 | 1/2001 | Binette et al. |
| 2005/0027482 A1 | 2/2005 | Benaoudia et al. |

(Continued)

FOREIGN PATENT DOCUMENTS

CA 2549576 A1 * 12/2006 ............... D21B 1/00

OTHER PUBLICATIONS

EPO, Extended European Search Report for corresponding European Patent Application No. 20755191.2, mailed Sep. 6, 2022, 6 pages.
(Continued)

*Primary Examiner* — Gabriel I Garcia
(74) *Attorney, Agent, or Firm* — NK Patent Law

(57) ABSTRACT

A computer implemented method is disclosed herein for monitoring and determining a quality level of incoming raw material from one or more sources. The method includes (1) receiving visual data associated with the incoming raw material; (2) determining an indication of quality level associated with the incoming raw material; and (3) transmitting, to at least one of a graphical user interface (GUI) and a computer log, the indication of quality level and at least one timestamp associated with the visual data. The visual data may include a plurality of images received from one or more cameras configured for monitoring the incoming raw material. A related system is also disclosed herein.

20 Claims, 3 Drawing Sheets

Related U.S. Application Data

(60) Provisional application No. 62/806,168, filed on Feb. 15, 2019.

(51) Int. Cl.
*G06F 16/51* (2019.01)
*G06F 16/583* (2019.01)
*G06Q 50/04* (2012.01)
*G06T 7/00* (2017.01)

(52) U.S. Cl.
CPC .......... *G06F 16/583* (2019.01); *G06Q 50/04* (2013.01); *G06T 7/0004* (2013.01); *G06T 2200/24* (2013.01); *G06T 2207/30161* (2013.01)

(58) Field of Classification Search
USPC ........................................... 382/141
See application file for complete search history.

(56) References Cited

U.S. PATENT DOCUMENTS

| | | |
|---|---|---|
| 2007/0158040 A1 | 7/2007 | Benaoudia et al. |
| 2008/0046209 A1 | 2/2008 | Ding |
| 2008/0140248 A1 | 6/2008 | Moore |

OTHER PUBLICATIONS

ISA/RU; International Search Report and Written Opinion for International Patent Application No. PCT/US20/18236 dated May 28, 2020, 8 pages.

WIPO; International Preliminary Report on Patentability for International Patent Application No. PCT/US2020/018236 dated Aug. 26, 2021, 6 pages.

CIPO; Office Action for corresponding patent application in Canada No. 3,130,393, dated Mar. 26, 2024, 4 pages.

\* cited by examiner

ONLINE METHOD TO DETERMINE QUALITY STANDARDS FOR INCOMING WOOD CHIPS TO A PAPERMILL

CROSS-REFERENCE TO RELATED APPLICATIONS

This application is a continuation of International Patent Application No. PCT/US20/18236, filed on Feb. 14, 2020, which claims the benefit of U.S. Provisional Patent Application No. 62/806,168, filed on Feb. 15, 2019, the entire contents of which are incorporated herein by reference.

TECHNICAL FIELD

The present invention relates generally to a manufacturing monitoring system, and more specifically, to a visual monitoring system configured to detect a quality level of incoming raw materials.

BACKGROUND

The greatest expense to integrated paper mills are the raw material wood chips that make up the pulp that later becomes paper at the reel of the machine. Off-line sampling of the chips provides less than 1% classification of the material. Chips that are off specification in size, wrong species or contaminated with bark and other foreign matter can greatly impact the subsequent paper making process.

The lack of chip quality data leaves the papermaker unable to make proactive process control decisions prior and during the lengthy process of converting chips to pulp. Additionally, vendors or internal suppliers that sell or provide these chips to the mill cannot be held to any penalty or feedback loop for supplying chips outside set quality standards.

Accordingly, a need exists for devices, systems and methods for providing feedback on one or more sources of a quality level of incoming raw materials (e.g. wood chips that are received for the process of making pulp during the paper manufacturing process). Additionally, other types of manufacturing processes may benefit from such devices, systems, and methods.

SUMMARY

This Summary is provided to introduce a selection of concepts in a simplified form that are further described below in the Detailed Description of Illustrative Embodiments. This Summary is not intended to identify key features or essential features of the claimed subject matter, nor is it intended to be used to limit the scope of the claimed subject matter.

Disclosed herein are methods, systems, and devices for solving the problem of providing feedback on one or more sources of a quality level of incoming raw materials for a manufacturing process. According to one embodiment, a method is implemented on at least one computing device for monitoring and determining a quality level of incoming raw material from one or more sources. The method includes (1) receiving visual data associated with the incoming raw material; (2) determining an indication of quality level associated with the incoming raw material; and (3) transmitting, to at least one of a graphical user interface (GUI) and a computer log, the indication of quality level and at least one timestamp associated with the visual data. The visual data may include a plurality of images received from one or more cameras configured for monitoring the incoming raw material. The method may further include storing the plurality of images in a database and transmitting an image of the plurality of images to the GUI upon request of a user of the GUI.

In some embodiments, the method further includes determining a source of the incoming raw material from a database using the at least one timestamp associated with the plurality of images and transmitting the source to the computer log. The incoming raw material may include a plurality of wood chips associated with a paper manufacturing process. Determining the indication of quality level may include processing the plurality of images to determine a thickness, an aspect ratio, a two dimensional size, a volume, a wood species, freshness factor, and/or a dryness level of a first chip of the plurality of wood chips. Determining the indication of quality level may further include processing the plurality of images to determine a defect quantity associated with the plurality of wood chips. The defect quantity may be associated with a composition of bark mixed with the plurality of wood chips.

In some embodiments, the method may further include receiving metadata associated with the paper manufacturing process and determining the indication of quality level may be further based on the metadata. The metadata may include at least one of a speed of the paper manufacturing process, a source of the plurality of wood chips, and a profile associated with the source of the wood chips. The profile may include at least one of a wood species parameter, a thickness parameter, an aspect ratio parameter, a two dimensional size parameter, a volume parameter, a composition of bark parameter, and a freshness factor parameter. The method may also further include transmitting a control signal upon determining the indication of quality level is unacceptable and the control signal may be configured to halt the paper manufacturing process In some embodiments, the at least one computing device may be coupled to the one or more cameras over at least one of a local area network (LAN) and a wide area network (WAN). The one or more cameras may include a thermal camera, a visible spectrum camera, an ultraviolet (UV) spectrum camera, an x-ray camera, or the like. The at least one computing device may be a portion of a networked computing environment and may be a cloud computing environment. In certain embodiments, the at least one computing device may be a virtualized server.

According to another embodiment, a computing device includes a memory and at least one processor configured to provide a method for monitoring and determining a quality level of incoming raw material from one or more sources. The method includes (1) receiving visual data associated with the incoming raw material; (2) determining an indication of quality level associated with the incoming raw material based at least partially on the visual data; and (3) transmitting, to at least one of a GUI and a computer log, the indication of quality level and at least one timestamp associated with the visual data. The visual data may include a plurality of images received from one or more cameras configured for monitoring the incoming raw material.

According to another embodiment, a non-transitory computer-readable storage medium stores instructions to be implemented on at least one computing device including at least one processor. The instructions when executed by the at least one processor cause the at least one computing device to provide a method for monitoring and determining a quality level of incoming raw material from one or more sources. The method includes (1) receiving visual data associated with the incoming raw material; (2) determining an indication of quality level associated with the incoming raw material based at least partially on the visual data; and (3) transmitting, to at least one of a GUI and a computer log, the indication of quality level and at least one timestamp associated with the visual data. The visual data may include a plurality of images received from one or more cameras configured for monitoring the incoming raw material.

BRIEF DESCRIPTION OF THE DRAWINGS

The foregoing summary, as well as the following detailed description of preferred embodiments, is better understood when read in conjunction with the appended drawings. For the purposes of illustration, there is shown in the drawings exemplary embodiments; however, the presently disclosed invention is not limited to the specific methods and instrumentalities disclosed. In the drawings.

DETAILED DESCRIPTION

The presently disclosed subject matter is described with specificity to meet statutory requirements. However, the description itself is not intended to limit the scope of this patent. Rather, the inventors have contemplated that the claimed invention might also be embodied in other ways, to include different steps or elements similar to the ones described in this document, in conjunction with other present or future technologies. Moreover, although the term "step" may be used herein to connote different aspects of methods employed, the term should not be interpreted as implying any particular order among or between various steps herein disclosed unless and except when the order of individual steps is explicitly described.

These sections may be present in some industrial processes such as that which may be found in a paper production facility, but the systems and methods disclosed herein are equally applicable to other industrial settings.

An online and real-time camera-based inspection system positioned to monitor the incoming wood chips from an incoming source can provide a breakdown of key wood chip parameters per time. Based on the time of inspection, the resulting classification can be tied back to the supplier (external or internal). The mill can then benchmark the actual chip quality parameter against set quality standards to determine corrective actions to provide optimum outcome of this raw material as it becomes paper. Additionally, wood chip suppliers can be financially penalized for supplying a quality level that is less than predetermined standards.

The resulting financial benefit for online and real-time chip inspection has several key impacts to the paper production facility including: (1) The overall cost of the raw material may be reduced by financially penalizing vendor supplying low quality wood chips. (2) The overall quality of incoming wood chips may be increased while maintain the same price point. (3) There may be more incentive for vendors to provide better wood chip quality. (4) Feedback may be provided directly to internal chip processes to correct and/or improve production processes. (5) By providing better wood chips the overall quality of the paper is improved and the capacity of the paper machines may be increased. (6) Less paper waste resulting from producing off specification product. (7) Less production downtime may result reducing the number of paper breaks. (8) And, paper production may be increased by increasing paper machine speed.

Figure 1:
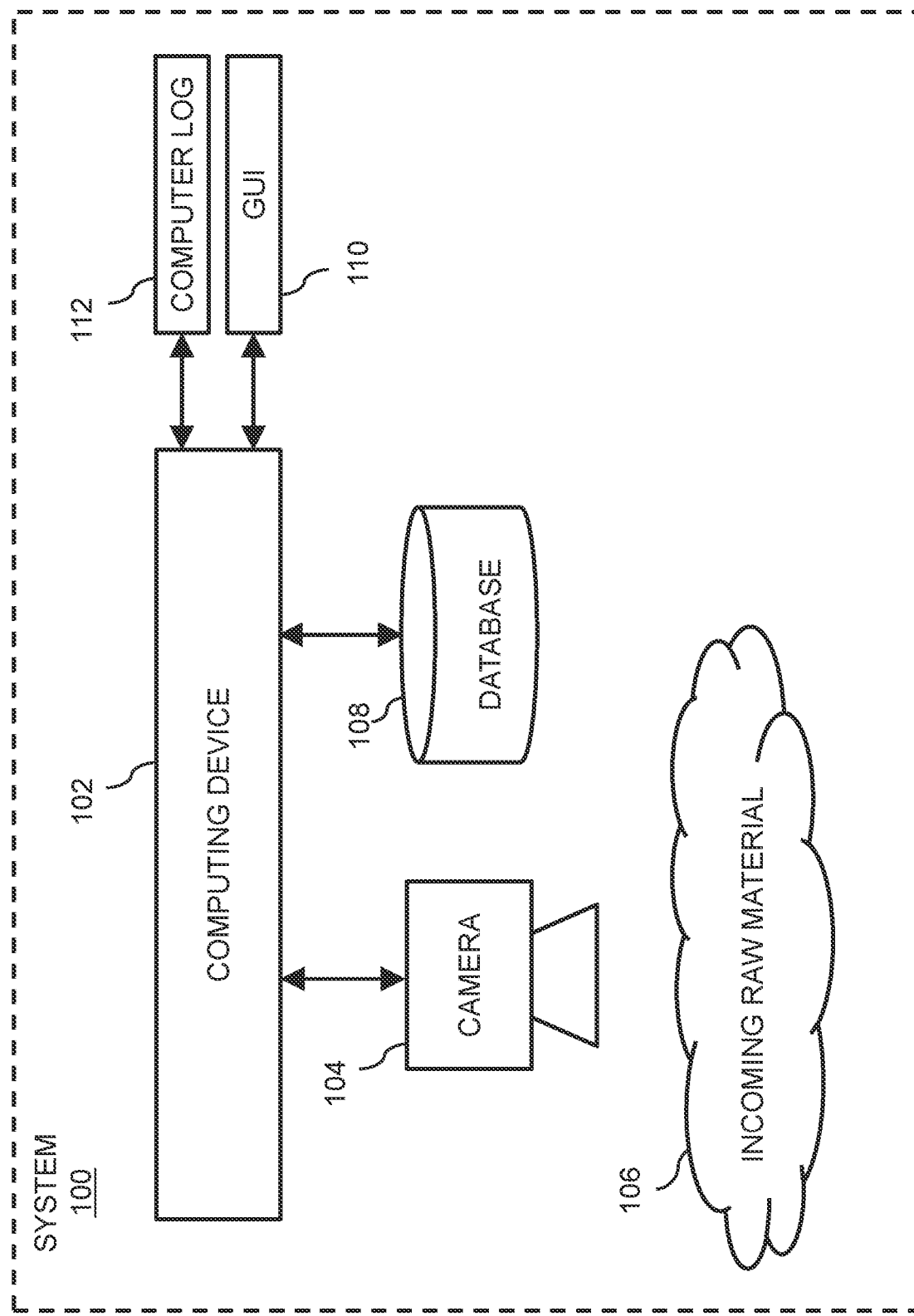
FIG. 1 depicts a system for monitoring and determining a quality level of incoming raw material from one or more sources in accordance with embodiments of the present disclosure.

FIG. 1 depicts a system 100 for monitoring and determining a quality level of incoming raw material from one or more sources. The system 100 includes a computing device 102 coupled with a camera 104. The camera 104 may be electrically or wirelessly coupled to the computing device 102; and may be coupled over a local area network (LAN) and/or a wide area network (WAN). In certain embodiments the WAN may be the Internet. The camera 104 is configured to monitor incoming raw material 106 for a manufacturing process. The manufacturing process may be a paper manufacturing process and the camera may be configured to capture images of wood chips associated with the paper manufacturing process. The paper manufacturing process may include any process steps from receipt of raw material (e.g. wood chips) through finished product.

The camera 104 may include one or more charge-coupled devices (CCDs) and/or one or more complementary metal-oxide semiconductors (CMOSs) for image capture. The camera 104 may be configured for various wavelengths alone or in combination with one another. The various wavelengths may include the visible spectrum. The camera 104 may be configured for shape analysis and classification in conjunction with the computing device 102. The various wavelengths may also include infrared (IR) spectrum and near IR spectrum. Using IR and near IR spectrum, the camera may be configured for determining moisture content and/or material density in conjunction with the computing device 102.

The camera 104 may be configured for thermal imaging and may be capable of measuring temperature changes as a function of active temperature modulation (e.g. to determine mass and/or moisture content of material using the computing device 102). The camera 104 may also be configured with one or more ultraviolet (UV) spectrum sensors and/or one or more x-ray sensors. The camera 104 may also be configured with active focus and be capable of focal plane sweeping. The camera 104 may be able to determine depth using various defocus applications in conjunction with the computing device 102. The camera 104 may also be a smartphone camera or the like. The camera 104 may also be plurality of cameras and may include one or more of the previously disclosed camera types, features, and/or functions. Additionally the computing device 102 may include one or more computing devices distributed between the one or more cameras and one or more distinct computing devices.

In some embodiments, the camera 104 may be configured to be used in combination with active and/or directional illumination devices (not shown in FIG. 1). For example the system 100 may be able to use contrast enhancement and determine shape-from-shading.

The system 100 may include a plurality of other sensors not shown in FIG. 1. For example, the system 100 may also include depth sensors to determine shape and structural analysis. The system 100 may also include time of flight sensors that include light detection and ranging (LiDAR)

and/or light emitting diodes (LED). The system 100 may also include one or more structured light projectors and/or sensors. The system 100 may also include binocular, trinocular, and/or other calibrated multi-camera depth rigs. The system 100 may also include light field cameras and/or moisture sensors (e.g. laser spectroscopy).

FIG. 1 also depicts a database 108. The database 108 is also coupled with the computing device 102 and may be electrically or wirelessly coupled. The database 108 may be coupled over a LAN and/or WAN. The database 108 may be configured to store records associated with purchases of the incoming raw material 106 and may also be configured to store captured images from the camera 104.

A graphical user interface (GUI) 110 and a computer log 112 is also coupled with the computing device 102. The GUI 110 and the computer log 112 may me coupled over a LAN or a WAN, and may be electrically or wirelessly coupled. The computer log 112 may be provided by the database 108. The GUI 110 may be provided by a workstation, a personal computer (PC), a mobile tablet, a smart phone, or the like. The GUI 110 may be configured to display at least a portion of the computer log 112. The computing device 102 may be configured to store the plurality of images in the database 108 and transmit an image of the plurality of images to the GUI 110 upon request of a user of the GUI 110. In some embodiments, both the GUI 110 and the computer log 112 maybe provided by the workstation, the PC, the mobile tablet, the smart phone, or the like.

The computing device 102 may be configured to process the captured images of wood chips using machine learning techniques. In certain embodiments, the captured images may be processed using deep learning techniques including using an artificial neural network. The artificial neural network may allow the computing device 102 to learn via an algorithm while processing additional image data. Via the machine learning and/or deep learning techniques, the computing device 102 may be able to determine from the stored captured images: a thickness, an aspect ratio, a two dimensional size, a volume, a wood species, a freshness factor, and/or a dryness level of one or more wood chips associated with the incoming raw material. For example, the wood species may be one of western hemlock (*Tsuga heterophylla*), balsam poplar (*Populus balsamifera*), eastern white pine (*Pinus strobus*), or the like. The freshness factor may include an estimated age and/or decay of the one or more wood chips. From this determination, a quality level may be determined of the one or more wood chips. In certain embodiments, a defect level and/or defect percentage of a plurality of wood chips may also be determined. For example, the defect quantity may be associated with a composition of bark mixed with the wood chips. The quality level and a timestamp associated with the stored capture images may be transmitted to and stored in the computer log 112. The computing device 102 may also determine a source of the wood chips using the timestamp and purchase records stored in the database 108.

Figure 2:
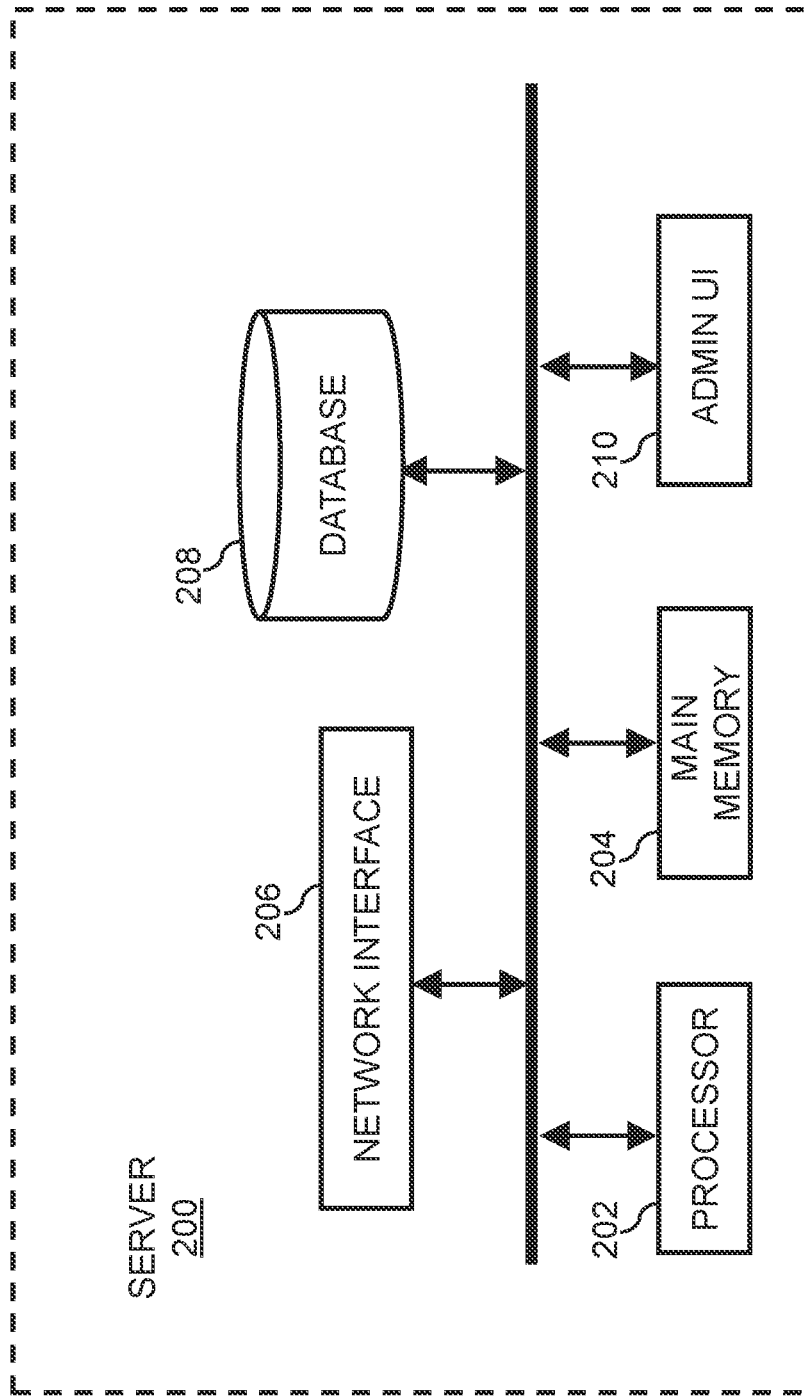
FIG. 2 depicts a block diagram of a server that provides a method for monitoring and determining a quality level of incoming raw material from one or more sources in accordance with embodiments of the present disclosure . . . .

The computing device 102 may be configured to receive metadata associated with the paper manufacturing process and determine the indication further based on the metadata. The metadata may include at least one of a speed of the paper manufacturing process, a source of the plurality of wood chips, and a profile associated with the source of the plurality of wood chips. The profile may include at least one of a wood species parameter, a thickness parameter, an aspect ratio parameter, a two dimensional size parameter, a volume parameter, a composition of bark parameter, and a freshness factor parameter. The computing device 102 may also be configured to transmit a control signal upon determining the indication of quality level is unacceptable and the control signal may be configured to halt the paper manufacturing process FIG. 2 depicts a block diagram of a server 200 that provides a method for monitoring and determining a quality level of incoming raw material from one or more sources. The server 200 may be configured to provide the computing device 102 of FIG. 1. The server 200 may include at least one of a processor 202, a main memory 204, a network interface 206, a database 208, and an administration user interface (UI) 210. In some embodiments the database 208 may be the database 108 of FIG. 1.

The processor 202 may be a multi-core server class processor suitable for hardware virtualization. The processor may support at least a 64-bit architecture and a single instruction multiple data (SIMD) instruction set. The main memory 204 may include a combination of volatile memory (e.g. random access memory) and non-volatile memory (e.g. flash memory). The network interface 206 may be configured to be coupled to one or more of the LANs and WANs described in FIG. 1. The database 208 may provide the computer log 112 of FIG. 1. The computing device 102 may be a portion of a networked computing environment, such as a cloud computing environment. The server 200 may be configured to host at least a portion of a virtual server and the method may be provided by the virtual server. The server 200 may be implemented in the Microsoft Azure®, the Amazon Web Services® (AWS), or the like cloud computing data center environments. In other embodiments, the server 200 may be locally installed in proximity with the manufacturing process.

Figure 3:
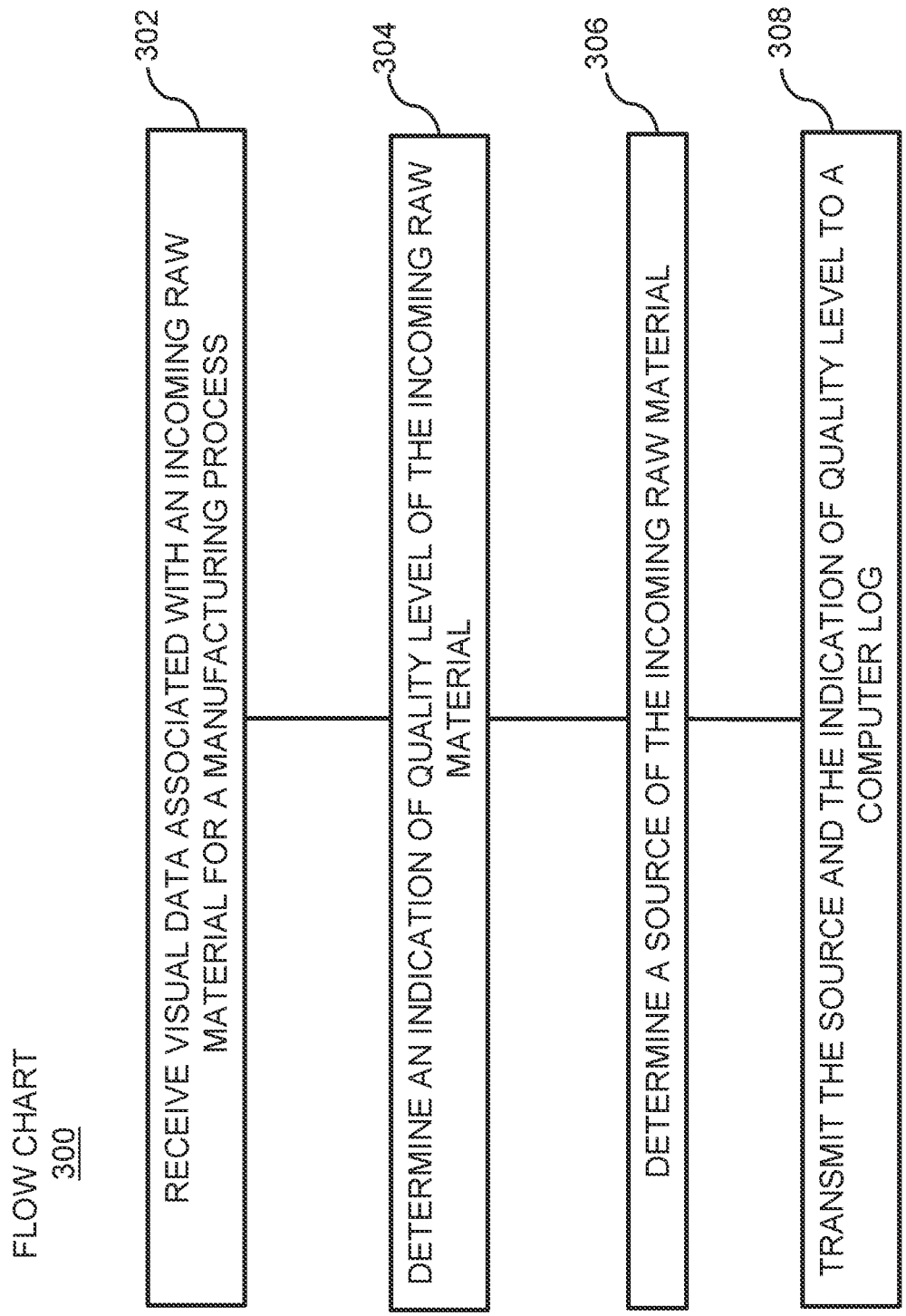
FIG. 3 depicts a flowchart illustrating a method for monitoring and determining a quality level of incoming raw material from one or more sources in accordance with embodiments of the present disclosure.

FIG. 3 depicts a flowchart 300 illustrating a basic method for monitoring and determining a quality level of incoming raw material from one or more sources. In step 302, visual data associated with an incoming raw material (e.g. wood chips) for a manufacturing process (e.g. a paper manufacturing process) is received. The visual data may be a plurality of images of wood chips captured by one or more cameras. In step 304, an indication of quality level of the incoming raw material is determined. The indication of quality level may be determined using machine learning and/or deep learning as previously described. In step 306, a source of the incoming raw material is determined. The source may be determined by using a timestamp associated with the images of wood chips and purchase records stored in a database. In step 308, the source and the indication of quality level is transmitted to a computer log. The computer log may be used to facilitate the manufacturing process and/or to provide feedback to one or more vendors of the incoming raw material.

The various techniques described herein may be implemented with hardware or software or, where appropriate, with a combination of both. These techniques may be embodied on the server 200 of the presently disclosed subject matter. Thus, the methods and apparatus of the disclosed embodiments, or certain aspects or portions thereof, may take the form of program code (i.e., instructions) embodied in tangible media, such as floppy diskettes, CD-ROMs, hard drives, or any other machine-readable storage medium, wherein, when the program code is loaded into and executed by a machine, such as a computer, the machine becomes an apparatus for practicing the presently disclosed invention. In the case of program code execution on programmable computers, the computer will generally include a processor, a storage medium readable by the processor (including volatile and non-volatile memory and/ or storage elements), at least one input device and at least one output device. One or more programs are preferably implemented in a high level procedural or object oriented programming language to communicate with a computer system. However, the program(s) can be implemented in assembly or machine language, if desired. In any case, the language may be a compiled or interpreted language, and combined with hardware implementations.

The described methods and apparatus may also be embodied in the form of program code that is transmitted over some transmission medium, such as over electrical wiring or cabling, through fiber optics, or via any other form of transmission, wherein, when the program code is received and loaded into and executed by a machine, such as an EPROM, a gate array, a programmable logic device (PLD), a client computer, a video recorder or the like, the machine becomes an apparatus for practicing the presently disclosed invention. When implemented on a general-purpose processor, the program code combines with the processor to provide a unique apparatus that operates to perform the processing of the presently disclosed invention.

While the embodiments have been described in connection with the preferred embodiments of the various figures, it is to be understood that other similar embodiments may be used or modifications and additions may be made to the described embodiment for performing the same function without deviating therefrom. Therefore, the disclosed embodiments should not be limited to any single embodiment, but rather should be construed in breadth and scope in accordance with the appended claims.

What is claimed:

1. A method implemented on at least one computing device for monitoring and determining a quality level of incoming wood chips from one or more sources in absence of off-line inspection, the method comprising:
   receiving real-time visual data from an online camera system configured to capture images on-line and in real-time of incoming wood chips associated with a paper manufacturing process;
   determining online and in real-time an indication of quality level associated with the incoming wood chips based on the real-time visual data and deep learning using an artificial neural network configured to learn an algorithm while processing additional image data; and
   transmitting, to at least one of a graphical user interface (GUI) and a computer log, the indication of quality level and at least one timestamp associated with the real-time visual data.

2. The method of claim 1, wherein the real-time visual data includes a plurality of images received from the online camera system.

3. The method of claim 2 further comprising determining a source of the incoming wood chips from a database using the at least one timestamp associated with the plurality of images.

4. The method of claim 3 further comprising transmitting the source to the computer log.

5. The method of claim 2, wherein determining the indication of quality level comprises processing the plurality of images to determine a thickness of a first chip of the incoming wood chips.

6. The method of claim 2, wherein determining the indication of quality level comprises processing the plurality of images to determine a wood species of a first chip of the incoming wood chips.

7. The method of claim 2, wherein determining the indication of quality level comprises processing the plurality of images to determine a dryness level of a first chip of the incoming wood chips.

8. The method of claim 2, wherein determining the indication of quality level comprises processing the plurality of images to determine a defect quantity associated with the incoming wood chips.

9. The method of claim 8, wherein the defect quantity is associated with a composition of bark mixed with the incoming wood chips.

10. The method of claim 2, wherein determining the indication of quality level comprises processing the plurality of images to determine an aspect ratio of a first chip of the incoming wood chips.

11. The method of claim 2, wherein determining the indication of quality level comprises processing the plurality of images to determine a two dimensional size of a first chip of the incoming wood chips.

12. The method of claim 2, wherein determining the indication of quality level comprises processing the plurality of images to determine a volume of a first chip of the incoming wood chips.

13. The method of claim 2, wherein determining the indication of quality level comprises processing the plurality of images to a freshness factor of a first chip of the incoming wood chips.

14. The method of claim 2 further comprising receiving metadata associated with the paper manufacturing process and determining the indication of quality level is further based on the metadata.

15. The method of claim 14, wherein the metadata comprises at least one of a speed of the paper manufacturing process, a source of the incoming wood chips, and a profile associated with the source of the incoming wood chips.

16. The method of claim 15, wherein the profile includes at least one of a wood species parameter, a thickness parameter, an aspect ratio parameter, a two dimensional size parameter, a volume parameter, a composition of bark parameter, and a freshness factor parameter.

17. The method of claim 2 further comprising transmitting a control signal upon determining the indication of quality level is unacceptable, wherein the control signal is configured to halt the paper manufacturing process.

18. The method of claim 2 further comprises storing the plurality of images in a database and transmitting an image of the plurality of images to the GUI upon request of a user of the GUI.

19. A computing device for monitoring and determining a quality level of incoming wood chips from one or more sources in absence of off-line inspection, the computing device comprising:
   a memory; and
   at least one processor configured for:
   receiving real-time visual data from an online camera system configured to capture images on-line and in real-time of incoming wood chips associated with an paper manufacturing process;
   determining online and in real-time an indication of quality level associated with the incoming wood chips based on the real-time visual data, and deep learning using an artificial neural network configured to learn an algorithm while processing additional image data; and
   transmitting, to at least one of a graphical user interface (GUI) and a computer log, the indication of quality level and at least one timestamp associated with the real-time visual data.

20. A non-transitory computer-readable storage medium, the non-transitory computer-readable storage medium storing instructions to be implemented on at least one computing device including at least one processor, the instructions when executed by the at least one processor cause the at least one computing device to perform a method of determining a quality level of incoming wood chips from one or more sources in absence of off-line inspection, the method comprising:

receiving real-time visual data from a online camera system configured to capture images on-line and in real-time of incoming wood chips associated with a paper manufacturing process;

determining online and in real-time an indication of quality level associated with the incoming wood chips based on the real-time visual data and deep learning using an artificial neural network configured to learn an algorithm while processing additional image data; and transmitting, to at least one of a graphical user interface (GUI) and a computer log, the indication of quality level and at least one timestamp associated with the real-time visual data.

* * * * *